US008730779B2

(12) United States Patent
Serr et al.

(10) Patent No.: US 8,730,779 B2
(45) Date of Patent: May 20, 2014

(54) TEST ELEMENT HAVING AN OPTICAL DATA STORAGE, DEVICE FOR READING THE OPTICAL DATA STORAGE OF THE TEST ELEMENT AND MEASURING SYSTEM THEREOF

(71) Applicant: Roche Diagnostics Operations, Inc., Indianapolis, IN (US)

(72) Inventors: Markus Serr, Speyer (DE); Dirk Voelkel, Djursholm (SE); Mandiaye Ndao, Strasbourg (FR)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/904,071

(22) Filed: May 29, 2013

(65) Prior Publication Data

US 2013/0258832 A1 Oct. 3, 2013

Related U.S. Application Data

(63) Continuation of application No. PCT/EP2011/006063, filed on Dec. 3, 2011.

(30) Foreign Application Priority Data

Dec. 8, 2010 (EP) .................................... 10015410

(51) Int. Cl.
*G11B 7/00* (2006.01)
(52) U.S. Cl.
USPC ......................................................... 369/103
(58) Field of Classification Search
USPC .................................. 369/103; 359/12; 430/2
See application file for complete search history.

(56) References Cited

U.S. PATENT DOCUMENTS

| 4,011,435 A | 3/1977 | Phelps et al. |
| 4,094,011 A | 6/1978 | Nagao |
| 4,820,006 A | 4/1989 | Constant |
| 5,644,412 A * | 7/1997 | Yamazaki et al. ................. 359/2 |
| 6,027,689 A * | 2/2000 | Markart ......................... 422/403 |
| 7,301,683 B2 * | 11/2007 | Tanaka .............................. 359/9 |
| 2008/0041955 A1 * | 2/2008 | Volkening et al. ............ 235/457 |
| 2009/0141612 A1 | 6/2009 | Mitsuya |

FOREIGN PATENT DOCUMENTS

| DE | 19806054 A1 | 8/1999 |
| JP | 07-230524 A | 8/1995 |
| JP | 2001-188459 A | 7/2001 |
| WO | 98/55963 A1 | 12/1998 |
| WO | 2007/107251 A1 | 9/2007 |

* cited by examiner

*Primary Examiner* — Brenda Bernardi
(74) *Attorney, Agent, or Firm* — Roche Diagnostics Operations, Inc.

(57) ABSTRACT

A test element is disclosed for analyzing a human or animal body fluid sample. The test element includes a substrate carrying a test field with a reagent for effecting a detection reaction when exposed to the body fluid sample, and an optical data storage in which data regarding the test element, preferably calibration data, is stored. Accordingly, the data storage is a holographic data storage. A hologram reader also is disclosed for reading the data storage of such a test element. Moreover, a hologram label and a method for manufacturing a hologram label are disclosed, as is a medical product including a holographic data storage in which data regarding the product is stored.

8 Claims, 9 Drawing Sheets

TEST ELEMENT HAVING AN OPTICAL DATA STORAGE, DEVICE FOR READING THE OPTICAL DATA STORAGE OF THE TEST ELEMENT AND MEASURING SYSTEM THEREOF

CROSS-REFERENCE TO RELATED APPLICATIONS

This patent application is a continuation of Int'l Patent Application No. PCT/EP2011/006063; filed 3 Dec. 2011, which claims the benefit of EP Patent Application No. 10015410.3; filed 8 Dec. 2010. Each patent application is incorporated herein by reference as if set forth in its entirety.

TECHNICAL FIELD

The invention relates generally to engineering and electro-chemistry, and more particularly to an analytical consumable such as a test element, namely a test strip or even a cartridge containing several test elements, and a device and system for measuring an analyte concentration in a body fluid sample with such an analytical consumable.

BACKGROUND

For testing blood, interstitial fluid or other body fluids, it is customary to use test elements carrying test fields with reagents that effect a detection reaction when exposed to a body fluid sample. The detection reaction, for example, can lead to fluorescence or a color change that can be analyzed by photometry to determine an analyte concentration such as the concentration of glucose, lactate or hematocrit. Also known are detection reactions for electrochemical measurements of an analyte concentration. In either case, the detection reaction leads to a change in a parameter that can be measured physically, whereby the intensity of the change depends on the analyte concentration to be measured.

Typically, detection sensitivity varies substantially between production batches of test elements containing the reagents. For this reason, there is a need to have calibration data to be able to determine the analyte concentration with high precision when analyzing the result of the detection reaction from the extent of the change of the physical parameter such as a change of color. Calibration data of this type usually is determined for each production batch using calibration liquids of known analyte concentration. The calibration data is stored on a data carrier that is jointly distributed with the test element. The user or patient then transfers the calibration data to a measuring device. This often leads to higher complexity of the overall process, lower compliance by the patient and is prone to error and manipulation.

Such calibration data also allows using test elements with different reagents or detection reactions for concentration measurements of different bodily fluids such as blood, blood plasma, serum, urine, saliva, semen, lymph, synovial fluid, amniotic fluid, lacrimal fluid, cyst fluid, sweat or bile with respect to a broad variety of analytes, such as glucose, lactate, hematocrit, cholesterol or peptides.

An approach to circumvent the need for calibration data is to optimize production with regard to tolerances, which is usually unfavorable with respect to production cost and leads to large amounts of rejections. The calibration data can contain the information that is necessary to determine the analyte concentration from the result of the detection reaction.

EP Patent Application Publication No. 1574855 describes a system having a barcode containing calibration information that is fixed to the outside of a drum cartridge containing several test elements. It also is known to print barcodes directly on test elements. An important aspect of barcode-based data storage disclosed in the document is that the drum magazine has to be located precisely to avoid reading errors.

Although optical data storage by means of a barcode is inexpensive, the reading process of barcodes is prone to errors. This is especially true for analytical test elements where users handle the test elements, which may impair barcodes by fingerprints or scratches. In the best case, an error may be detected and the reading process repeated. Conversely, and in the worst case, erroneous calibration data is used that may cause incorrect measurement results. Moreover, standard barcode readers are rather large and require either a movement of the barcode or a scanning optic for a reading process.

Int'l Patent Application Publication No. WO 2008/151726 discloses cartridges carrying electronic or magnetic data storages such as electrically erasable programmable read-only memory (EEPROMS), radio-frequency identification (RFID) tags, smartcards or memory chips. With these storage devices, calibration data stored therein can be more reliably retrieved. However, this advantage is offset by higher costs and impractical for consumables for single use such as, for example, single test elements. For the foregoing reasons, additional means of storing and retrieving information such as calibration data on an analytical consumable are needed.

BRIEF SUMMARY

An object of this disclosure therefore is to show how calibration data can be stored inexpensively on an analytical consumable such as a test element and subsequently reliably retrieved. This object is met by a test element for analyzing a human or animal body fluid sample. The test element can include a substrate carrying a test field with a reagent for effecting a detection reaction when exposed to the body fluid sample. The test element also includes an optical data storage in which data regarding the test element is stored, where the optical data storage is a holographic data storage.

Accordingly, holograms can be used as an optical storage medium to, for example, store calibration data and other data related to a test element. It further can store even more general data related to a medical product such as data related to a production date or a manufacturing process of the test element or medical product, an expiration date, general information related to the medical product such as mode of use, dosage regimen, warnings or contact information and the like. Computer-generated holograms can be provided at low cost on the test element and can be read with small, inexpensive readers that can be readily integrated into a measuring device. Most importantly, holograms are fairly robust against dirt, scratches and fingerprints and need no precise positioning to be reliably read by readers. Both the positioning of the hologram on the test element and the positioning of the test element in the measuring device allow rather large manufacturing tolerances.

Holographic data storage can contain data in a binary encoded format in, for example, a two-dimensional dot matrix. Binary-encoded data is machine-readable but cannot be accessed without a reader. Holographic data storage therefore offers the advantage that the information stored cannot be read visually without the help of a specific hologram reader, which prevents false readings or interpretations by the user. It also is possible to combine a hologram storing binary-encoded data as described herein with another hologram, which can be read visually, for example, for anti-counterfeit purposes.

These and other advantages, effects, features and objects of the invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

While the present invention is susceptible to various modifications and alternative forms, exemplary embodiments thereof are shown by way of example in the drawings and are herein described in detail. It should be understood, however, that the description of exemplary embodiments that follows is not intended to limit the invention to the particular forms disclosed, but on the contrary, the intention is to cover all advantages, effects, features and objects falling within the spirit and scope of the invention as defined by the embodiments above and the claims below. Reference should therefore be made to the embodiments above and claims below for interpreting the scope of the invention. As such, it should be noted that the embodiments described herein may have advantages, effects, features and objects useful in solving other problems.

DESCRIPTION OF PREFERRED EMBODIMENTS

The test elements, measuring devices with hologram readers and measuring systems now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the test elements, measuring devices and measuring systems described herein will come to mind to one of skill in the art having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Holograms and Holographic Data Storage

In the literature, the word hologram is sometimes used for the image that is created by illuminating a holographic recording medium and sometimes for the holographic recording medium storing the image information. As used herein, "hologram" refers to the latter meaning.

When a hologram is illuminated with a laser beam, the beam is diffracted such that a diffracted beam contains the holographic image that then can be captured by an optical sensor such as a complementary metal-oxide-semiconductor (CMOS) or charge-coupled device (CCD) sensor. A hologram can be understood as a pattern that creates a holographic image by diffraction of coherent light. For historical reasons, this pattern often is called an interference pattern. Nowadays, such a pattern need not be created by actual interference of separate beams of coherent light, but can be calculated (i.e., computer-generated) and written digitally on a recording medium. Such holograms are called digital holograms. In any way, the pattern consists of pixels. In the case of a computer-generated hologram, the pixels are arranged in parallel lines.

In the case of a binary hologram, there are only two kinds of pixels in, for example, a relief hologram—pits and lands (i.e., reflecting pixels placed on two different elevation levels). In principle, a computer-generated hologram also can consist of three or more kinds of pixels. For example, a surface relief hologram may have reflecting pixels placed on four or more different elevation levels. The diffraction efficiency of a surface relief hologram can be increased if a larger number of different elevation levels is used. For example, a digital surface relief hologram may have pixels on 8 or more, 16 or more, or even more than 32 elevation levels. Even a digital surface relief hologram that has pixels on 256 or more elevation levels can be produced at rather low costs comparable to the cost of writing a DVD. More than 512 different elevation levels usually offer no significant improvement, but increase manufacturing costs. In one embodiment, a digital surface relief hologram may have pixels on 8 to 256 or alternatively on 64 to 256 elevation levels.

The holographic data storage used herein may have pixels arranged in straight lines parallel to each other like the pixels of a common computer screen. Alternatively, the pixels of the holographic data storage can be arranged in sections of parallel arcs. In this manner, much lower production costs can be achieved. This is because a large part of the production costs of holograms is caused by the need to produce a hologram master that can be used to replicate the hologram as often as desired. A low-cost production of a master can be achieved by writing on a rotating disc. This process is known from the production of masters for imprinting DVDs, CDs and the like. Accordingly, this technology also can be used to write the pixels of a hologram, which are thereby written in sections of circular arcs. The circular arcs may be sections of a spiral according to a common way of writing on an optical disc or may be sections of geometrically exact circles if the pixels are written on the disc circle by concentric circle like bits are sometimes written on magnetic discs.

It is important to note that the area of a hologram or the holographic memory need not be circular at all as an area of any shape such as a square, rectangle, triangle or other geometrical form is possible, as well as circle, oval or irregular and may be adapted to the requirements of the consumable to which it is attached, can be cut from a disk that provides an annular writing area.

Test Elements Having Holographic Data Storage

A test element for analyzing a sample of a human or animal body fluid sample can be cost-efficiently produced by a method including the steps of arranging a test field on a substrate, writing at least one hologram master on a rotating disc and then copying it onto a drum, using the drum for writing a series of hologram copies onto a strip that may be cut into labels that may be fixed on the test element. The test element then has a holographic data storage that consists of pixels arranged in parallel arcs.

When the hologram master is copied onto the drum, it may be inverted such that the pattern on the drum is a photographic negative of the hologram master (i.e., a pit of a hologram master on the disc is a land on the drum, and a land on the disc is a pit on the drum). As used herein, "copy" encompasses both an inverted copy and a non-inverted copy.

Various kinds of holograms may be used to store data. Especially well-suited holograms for use herein are surface relief holograms, which may be provided as labels that can be fixed on a test element or a medical product. Methods of manufacturing surface relief holograms are disclosed in, for example, U.S. Pat. No. 4,758,296. As such, the hologram may be on a label that is fixed on the test element or medical product by, for example, lamination, or it may be embossed into the substrate of the test element by, for example, hot stamping. The latter method offers a possibility to attach the desired data to the test element or medical product in a non-detachable way.

Holograms can store a rather large number of bits in a comparatively small area. An advantageous refinement herein uses this property to improve the reliability of data retrieval in that the holographic data storage comprises a multitude of identical holograms each containing identical calibration data as, for example, a digital (e.g., binary) matrix similar to a two-dimensional bar code. Thus, even if dirt, scratches or the like damages some holograms, data retrieval is not affected as long as there are undamaged holograms left for creating the holographic image (e.g., a digital matrix).

For example, the holographic data storage may comprise more than 10, more than 100, or over 1,000 holograms each containing identical calibration data. Although the holographic data storage may contain a much larger number of holograms, it is usually not economical to include more than 10,000, especially more than 100,000 holograms, in the holographic data storage. Considering the economic aspect, as well as the resulting size of the holograms, the holographic data storage can include 100 to 10,000 holograms or alternatively 1,000 to 5,000 holograms. In this manner, the holograms may contain redundant data such as checksum or parity bits so that any reading errors may be detected and corrected. Self-error detection and correction is very advantageous for a measuring device.

Such holographic data storage can be read by using a laser beam that illuminates only a fraction of the total area of the data storage. In principle, it suffices if the size of the spot illuminated by the laser beam is so large that it contains at least a single hologram. More reliable reading is possible if the spot covers several holograms. The number of holograms covered by such a spot depends on the diameter of the laser beam and the size of a hologram. The images of these holograms are then superimposed on a sensor of the reading device. Usually, the cross-sectional area of the laser beam for reading should be at least 5 times or even at least 10 times as large as the area of a hologram. For example, the laser beam for reading can illuminate a spot size containing less than 500 holograms (e.g., 10 to 100 holograms or alternatively 10 to 50 holograms).

An advantageous refinement herein is that the individual holograms are shaped as sections of an annulus. Such a shape can be achieved as a consequence of writing a hologram master on a rotating disc as explained above. The sections of an annulus need not be created by cutting the annulus along radial lines. The two lines intersecting the inner and outer circle of the annulus may have any shape and may even be parallel to each other.

The rotation speed of the disc may be varied during the writing process. If the speed of rotation and the number of pixels written per second is constant, the resulting hologram has the shape of a section of an annulus created by cutting along radial lines. By increasing the speed of rotation for writing circles with a larger radius, the angle between the lateral boundaries of the hologram can be increased. By matching the speed of rotation to the radius of the circle on which pixels are written, the shape of the hologram may even be a section of an annulus delimited by parallel lines.

As already described, the holographic data storage itself may have any shape even if the holograms are shaped as sections of an annulus. If a sufficiently large number of holograms, each with identical information, is used for the holographic data storage, cost-efficient production is possible as a continuous strip that then can be cut into individual labels to provide the holographic data storage. The continuous strip can be laminated lengthwise onto a continuous band or tape, which then can be cut transversely into individual test elements.

The application of a holographic data storage can be easily integrated into conventional manufacturing processes of test elements as described in, for example, U.S. Pat. No. 6,207,000. In this manner, the continuous strip is cut into labels that are already laminated to a test element. Of course, it also is possible to cut the strip of holograms first and then attach individual labels to individual test elements. The edge of the data storage may well cut through some of the holograms without adverse effect. There are still enough undamaged holograms left in the holographic data storage if they are small enough in comparison to the total of the holographic data storage. For example, the holographic data storage may have a total area of about 2 to 100 mm$^2$ or alternatively about 5 to 10 mm$^2$, and consist of holograms that each have a size of about 2,000 to 100,000 μm$^2$ or alternatively about 7,000 to 80,000 μm$^2$.

The holographic data storage can contain an adjustment signal to facilitate adjusting a reading device for reading the hologram. Such an adjustment signal can greatly facilitate the reading and processing of data. For example, the adjustment signal may be used to calculate the right power of a laser used for reading to read the signal with the best quality. By adjusting the output of a reading laser, the signal-to-noise ratio and contrast can be improved.

An advantageous refinement herein is to arrange the holographic data storage adjacent to another hologram for visual use as, for example, an anti-counterfeiting hologram showing a manufacturer's logo. The holographic data storage and the human-readable hologram can be replicated in a single step by combining two different hologram masters. Integrating holographic data storage and a human-readable hologram therefore is an inexpensive way to improve a consumable such as a test element.

A test element as described herein may be a single test element or a cartridge containing several test elements. Such test elements and a reading device into which the test elements are inserted for a measurement of an analyte concentration in a body fluid sample form a measurement system, as will be described in greater detail below.

Measuring Devices and Hologram Readers

A measuring device includes a measuring unit for measuring a result of a detection reaction caused by exposure of a test field of a test element to a body fluid sample, a hologram reader for reading a holographic data storage of the test element, and a holder for holding the test element in a reading position for reading its holographic data storage.

The hologram reader for such a measuring device includes an optical sensor with an array of sensitive elements and a coherent light source such as, for example, a laser. The hologram reader also can include a collimating lens that is arranged in an optical path for outgoing light emitted by the laser and in an optical path for incoming light to the sensor. When a hologram is read with the reader, a beam emitted by the laser passes through the collimating lens to the hologram. The hologram reflects and diffracts the beam and thereby creates a beam containing the hologram's image. This image beam then passes through the collimating lens on its way to the sensor.

The hologram reader may include a stack of several layers that are bonded together to form an optical system comprising the collimating lens and other optical elements like apertures and spacers. Each optical element can be provided as a layer of the stack. The layers are connected with each other to form the stack. The optical sensor can be connected to a bottom side of the stack. A very compact and small reader can be achieved by integrating the laser in the stack. For example, the sensor may be covered by a protective layer. On this layer, but to the side of the active sensor area, the laser may be placed. The remaining area of the protective layer, especially above the active sensor area, may be covered by a transparent spacer layer. The collimating lens can be placed above the laser and the spacer layer, either directly on top of them or with other layers in between. The laser may be covered by a beam-shaping lens for narrowing the angle of beam spread.

Such an optics stack has a sandwich structure and can be manufactured with very small tolerances by wafer handling. Instead of using conventional molding techniques to form individual lenses and other optical elements, wafer level lens surfaces can be made from wafers of transparent material. Lenses, especially Fresnel lenses, may be formed on wafer surfaces by direct-etching or replication. In this manner, all optical functions needed in the reader can be implemented by using a planar manufacturing approach.

In the direct-etch method, a resist is patterned on a wafer with conventional semiconductor lithographic techniques. The resist is then reflowed to form hemispherical shapes, and the wafers are dry-etched, transforming the hemispherical resist shape into the wafer material. A discrete approach also is possible by using several quantization levels and binary masks.

In the replication method, a master wafer is created as a mold. A replication material polymer is deposited on one or both sides of the transparent wafer, and the master wafer is brought into contact with the replication material that is cured, thus forming the lens surface.

After lens formation by either direct-etching or replication, multiple wafers are bonded together to form a wafer stack. Alignment marks may be placed on each wafer with conventional photolithographic tools, and an adhesive, for example, a thermally or UV-cured resin, can be used for bonding. After bonding several wafers together, they may be cut into individual optic stacks. These stacks are then each bonded to a sensor that can be attached to a printed circuit board by, for example, a ball grid.

The described wafer level approach makes it possible to provide a hologram reader that can be easily integrated into a small handheld measuring device such as for measuring glucose levels in blood.

An advantageous refinement herein is that the hologram reader comprises at least two lasers for illuminating different spots on a holographic memory. In this manner, a holographic data storage comprising a plurality of holograms containing identical information can be more reliably read. A single beam might hit an area of such a holographic data storage that contains no readable holograms. With two or even more beams hitting different spots of a holographic data storage the chances that at least one readable hologram is hit are greatly increased. In principle, it also is possible to use only a single laser to create two beams for illuminating different spots of the holographic data storage. However, it is usually easier to use several lasers. The lasers preferably are used one after the other for reading.

As mentioned above, the holographic data storage may be created by copying a hologram master continuously onto a strip. A series of copies is thereby created that follow consecutively one after the other. If a beam hits a joint between two such copies, it illuminates a part of either copy. As each copy of the hologram master contains a plurality of holograms storing identical information, the beams usually illuminates several holograms of either copy. Although illuminating several holograms of the same copy improves the image and therefore facilitates the reading process, illuminating holograms of adjacent copies usually blurs the image. This is because each hologram from the same copy causes an image that interferes constructively with the other images of holograms from that copy. This is not the case with images of holograms from adjacent copies as the images of holograms from different hologram master copies usually interfere destructively due to differences in phase.

If the quality of an image is too poor due to this effect, a possible remedy is to repeat the reading attempt by illuminating a different spot with, for example, a second laser. Another possible remedy is to create the holographic data storage by copying two different hologram masters alternately onto a strip, each hologram master containing a plurality of holograms storing identical data regarding the consumable. The hologram masters differ such that illuminating their holograms, or holograms of their copies, with a given beam causes the images to appear in two different locations. For example, the image of holograms of the first hologram master may appear in a first half of a sensor (e.g., its left half), and the image of holograms of the second hologram master in a second half of a sensor (e.g., its right half). Consequently, the use of two hologram masters causes a loss of information density of one half as each half of the sensor area is used for reading the same information. But the use of two such holograms masters greatly increases the reliability of the reading process even without a second laser.

Such a holographic data storage comprises a plurality of holograms, each of which contain identical data regarding the consumable, where the plurality includes holograms of a first kind and holograms of a second kind, and where illumination of holograms of the first kind causes an image in a first location and illumination of holograms of the second kind causes an image in a second location. For manufacturing, two hologram masters are used, a first hologram master containing holograms of the first kind and a second hologram master containing holograms of the second kind. These hologram masters are copied alternatingly onto a strip that may then be cut into individual labels. Then, even if a laser beam illuminates a spot that contains part of a copy of the first hologram master and part of a copy of the second master, stored information can be read easily. This is because all holograms contained in the copy of the first master, are holograms of the first kind that cause an image in a first half of a sensor or on a first sensor, whereas all holograms contained in the copy of the second master, are holograms of the second kind that cause an image in a second half of a sensor or on a second sensor. Hence, destructive interference between images from adjacent hologram master copies can be avoided.

Measuring Systems

A system for measuring an analyte concentration in a human or animal body fluid sample includes a test element as described above and a measurement device as describe above. The test element includes a test field with a reagent for effecting a detection reaction when exposed to the body fluid sample and a holographic data storage. The measuring device includes a measuring unit for measuring the result of a detection reaction caused by exposure of a test field of such a consumable to the body fluid sample and a hologram reader, preferably a layered hologram reader as described above, which is adapted for reading the holographic data storage of the test element.

An advantageous refinement herein is that the holographic data storage comprises a plurality of holograms each storing identical information, preferably at least 100 bits or alternatively at least 150 to 1500 bits. Each hologram covers only a fraction of the area of the holographic data storage. For reading information from the holographic data storage, it is sufficient if a fraction of the holographic data storage is illuminated by a laser beam. In principle, it is sufficient if a laser beam illuminates a single hologram. If the diameter of the laser beam is larger so that several holograms are illuminated, the reading process is even more reliable, as the laser beam creates a holographic image for each hologram. Such holographic images all contain the same information (e.g., a dot-matrix) and are superimposed on the sensor.

During the reading process, the laser beam preferably illuminates a spot on the holographic memory that is large enough to contain a plurality of holograms, for example, 10 or more holograms or alternatively 20 to 40 holograms. In some embodiments, the spot size is only a fraction of the area of the holographic data storage, for example, less than a fifth or alternatively less than a tenth. Especially useful are spot sizes of 0.5% to 5% of the total area the holographic data storage.

Additional Methods and Products

The inventors have realized that the holographic data storage described above with respect to a consumable such as a test element for analyzing a human or animal body fluid sample also may be used for other products. As such, the invention also refers to a method for manufacturing a hologram label storing digitally encoded information, for example, product related data, like a batch information or manufacturing data. The method is characterized in that at least one hologram master is written on a rotating disc and then copied onto a drum, the drum is used for writing a series of hologram copies onto a strip, and the strip is cut into labels. Such a label may be fixed to a product to provide machine-readable information about the product.

The product can be a medical product. The holographic data storage of the product can contain batch specific data, like calibration data or manufacturing data, for example, a manufacturing or a use-by date. In general, the holographic data storage may contain any information usually provided on a package insert. In some instances, the medical product comprises a packaging that is provided with the holographic data storage. The holographic data storage can be, for example, a hologram label as described herein above that can be attached to the medical product. Alternatively, the holographic data storage can be imprinted directly in the medical product on, for example, the packaging of a medical product such as medicine. Likewise, the holographic data storage can be imprinted directly on a blister pack, which may, for example, contain pills, or on a sterility pack of other medical products such as syringes, infusion bottles, kits, etc. as long as the material is suitable for imprinting a hologram.

This has the advantage that the holographic data storage cannot be removed from the medical product, at least not without destroying the package so that the removal cannot be unnoticed.

The medical product may be a medicine such as a pill, liquid or topical, a medical apparatus, or a consumable for a medical apparatus. The medicine may be provided in a blister pack, bottle or tube. The medical apparatus may be a measurement device or an apparatus for therapeutic or surgical treatment. Consumables for such apparatuses may be test elements, chemical products like test substances or reagents, filters, lancets, syringes and the like.

The invention also refers to a label comprising a holographic data storage containing data in a digital, preferably binary, format, characterized in that the holographic data storage is written by pixels that are arranged along sections of parallel arcs, preferably concentric circular arcs. Any features of the holographic data storage described herein with respect to a consumable for analyzing a sample of a human or animal body fluid may also be present in the holographic data storage of such a label.

Advantageously, a label comprising a holographic data storage can be used to store information like batch-specific data including, for example, a manufacturing or use-by date or calibration information about the product to which the label is fixed. The label can be attached to a product or a packaging by an adhesive such as an acrylic adhesive, by welding or the like. Suitable adhesives may be heat activated or pressure sensitive adhesive, especially for permanent adhesion. As described above, the labels can be attached in a way that they cannot be removed from the medical product labeled therewith without destruction of the package or without the removal can be unnoticed.

EXAMPLES

Figure 1:
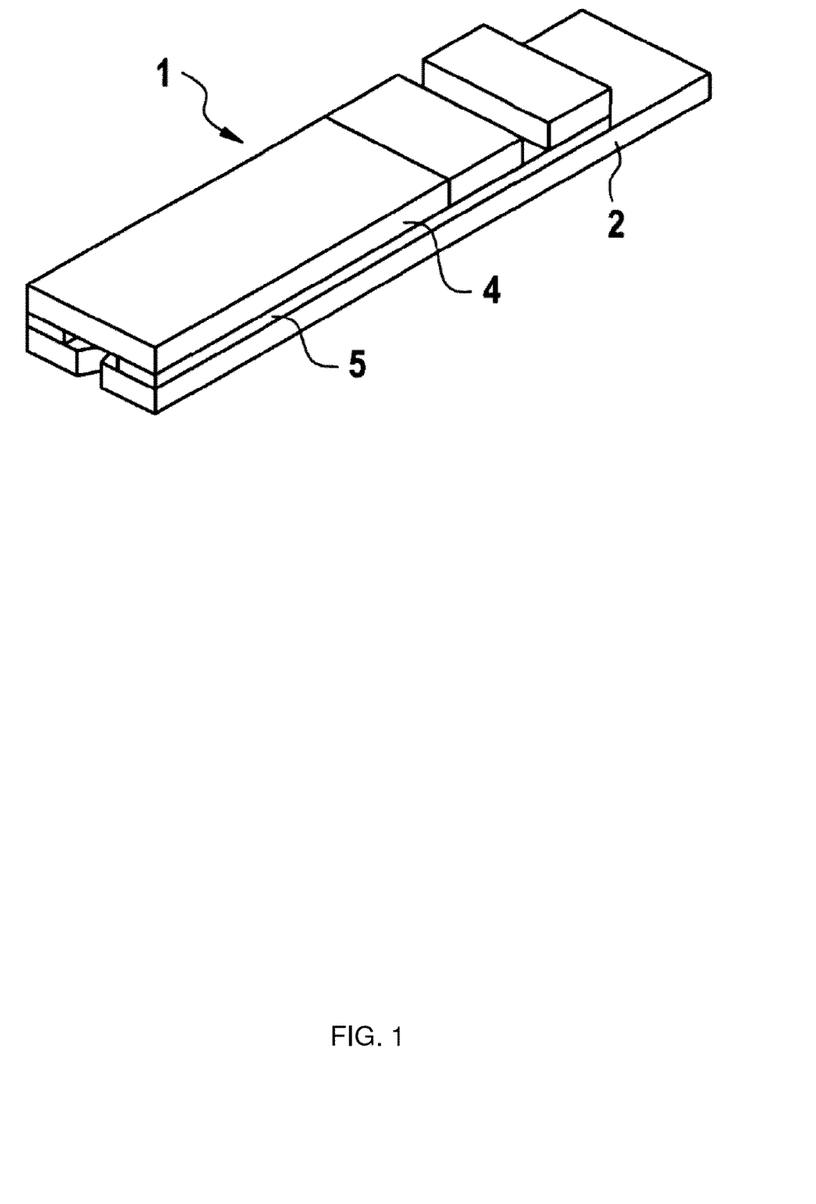
FIG. 1 shows an example of a test element for analyzing a sample of body fluid.
Figure 2:
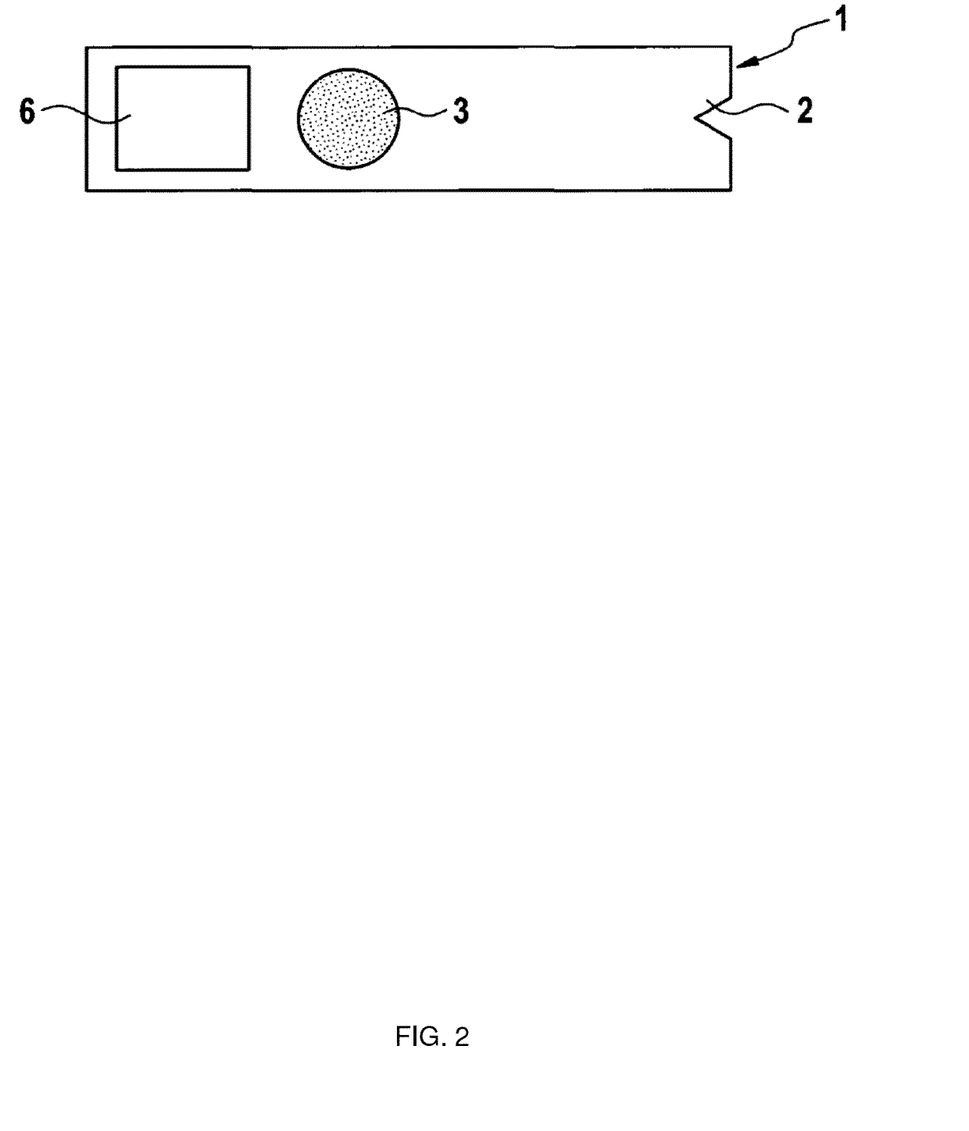
FIG. 2 shows a back view of the test element shown in FIG. 1.

FIGS. 1 and 2 show the front and back sides of a consumable 1 configured for analyzing a human or animal body fluid sample. The consumable shown is a test element in the form of a strip. Such test elements are used for measuring an analyte concentration in a body fluid sample, such as the concentration of glucose or any other medically significant analyte.

The test element 1 has a substrate 2 on which a test field 3 with reactants for effecting a detection reaction is arranged. The detection reaction may involve, for example, a change of color that can be analyzed by photometry to determine the analyte concentration of a body fluid sample applied to the test field 3.

The test element 1 may have a capillary channel for transporting the body fluid sample to the test field 3. In the example shown, such a capillary channel is provided between the substrate 2, a cover film 4 and a spacer 5 providing lateral walls of the channel. A capillary channel also may be provided by other means and is not strictly necessary for a test element for analyzing the body fluid sample.

On one of its sides, the test element 1 is provided with a holographic data storage 6 storing digitally encoded information. In the holographic data storage 6, a calibration information and/or any other information about the test element is stored, like data about the manufacturing process or the type of test element. The holographic data storage is provided as relief holograms.

Figure 3:
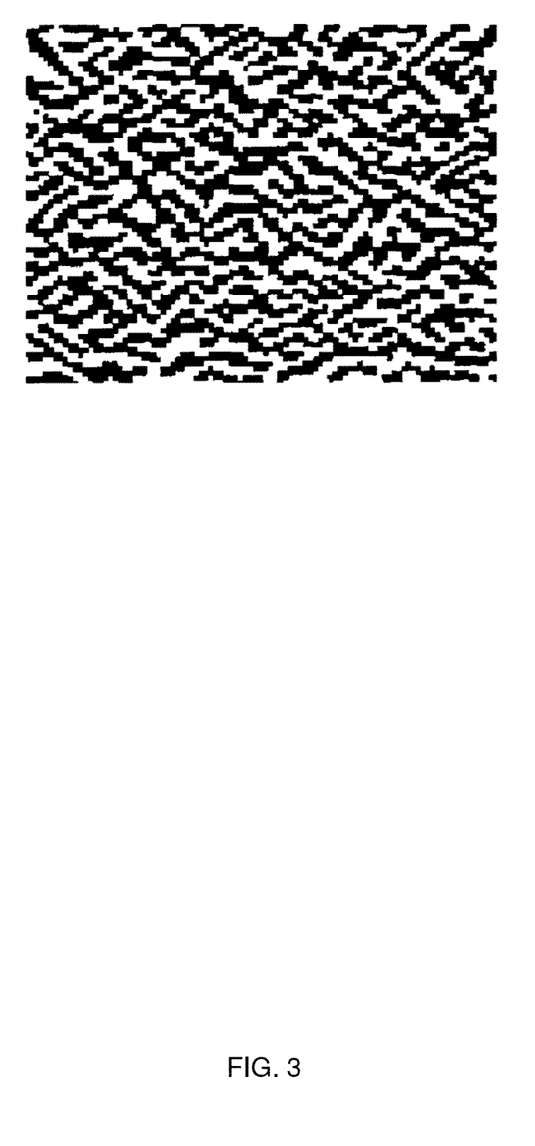
FIG. 3 shows schematically an example of a hologram consisting of straight lines of pixels.

FIG. 3 shows schematically an example of a rectangular hologram. The hologram shown in FIG. 3 is a binary hologram consisting of pixels arranged in straight parallel lines.

Figure 4:
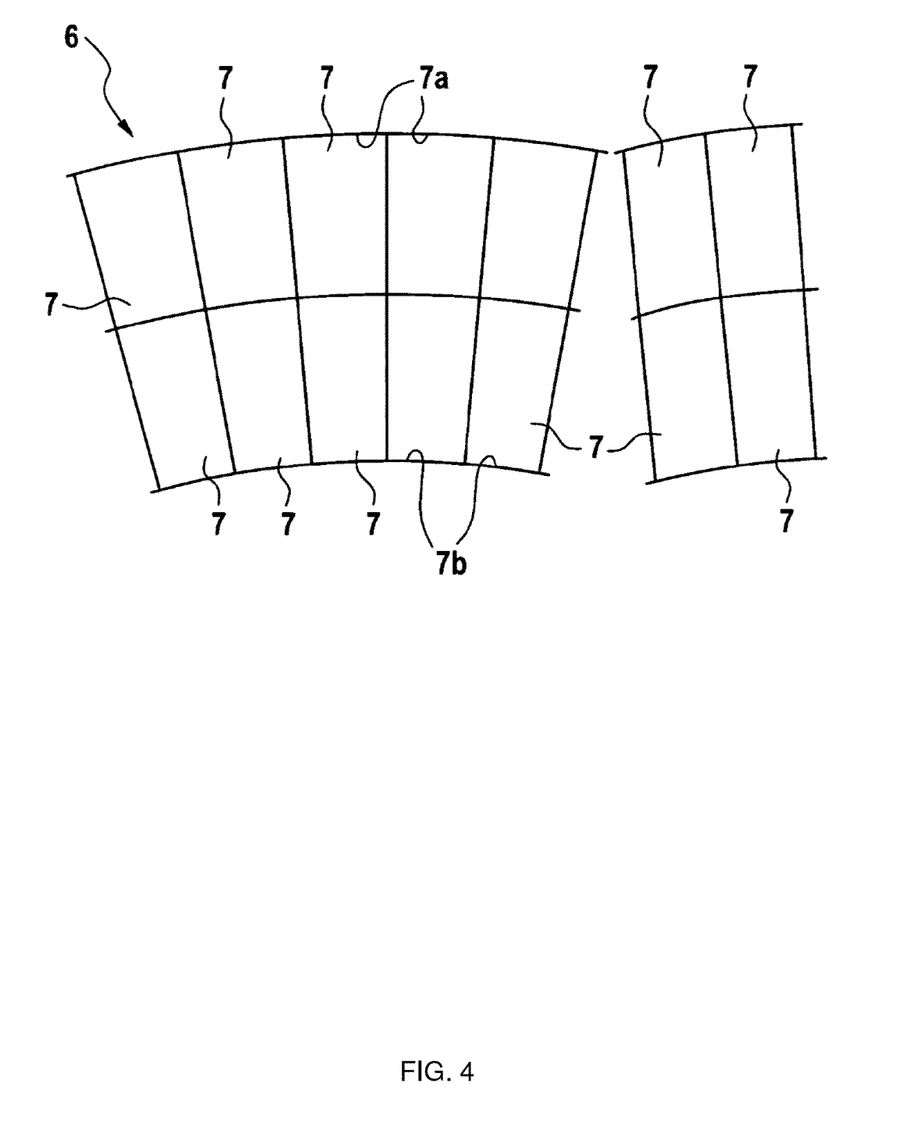
FIG. 4 shows schematically a detail of the holographic data storage of the test element shown in FIG. 2.

FIG. 4 shows schematically a detail of an example of a holographic data storage of a test element 1. The holographic data storage consists of a large number of identical holograms 7. Each of these holograms 7 is shaped as a section of an annulus. This means that it has an upper border 7a shaped as a section of a circular arc and a lower border 7b shaped as a section of a circular arc. These arcs are concentric. The lateral borders of the holograms 7 are straight lines.

Figure 5:
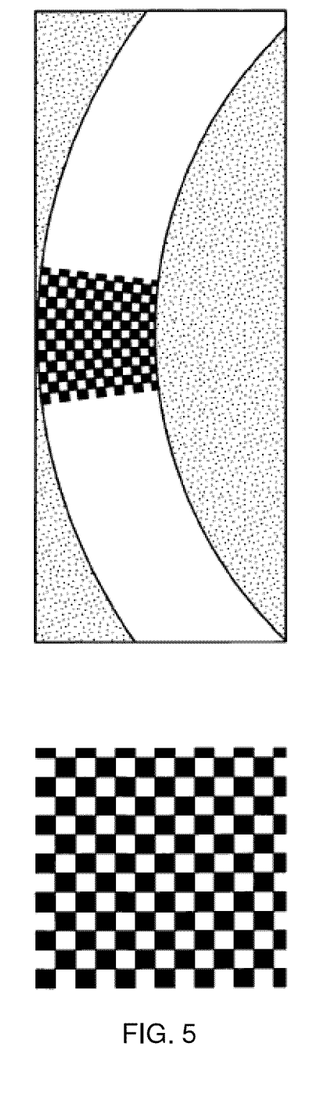
FIG. 5 shows schematically how the lines of pixels can be changed when a hologram is written on a rotating disc.

FIG. 5 shows schematically how the shape of a rectangular hologram is changed when written on a rotating disc. In FIG. 5, pixels are alternating in black and white to show how a rotating disc affects the lines along which the pixels are written. Of course, a hologram usually has a more complicated sequence of pixels as is shown in FIG. 3. Each pixel may have a size of about 0.4 to 2 $\mu m^2$, but a hologram also may be written with smaller or larger pixels.

The holograms 7 of FIG. 4 consist of several lines of pixels. Each line is a section of an arc. Such holograms can be created by means of a hologram master that is written onto a rotating disc. In this manner, the pixels of the hologram master are written on parallel lines that are each shaped as a section of a circular arc. Cost-efficient production is possible as there is a mature technology for writing binary pixels on optical discs like DVDs, for example. Instead of writing pixels as pits and lands on only two different elevation levels, pixels also may be written on a larger number of different elevation levels. In this manner, a digital surface relief hologram with improved diffraction efficiency may be provided. For example, the digital surface relief hologram may have pixels on up to 8 or up to 16 elevation levels. Especially good results can be achieved with pixels on 128 to 512 elevation levels.

Pixels may be written along a spiral on the disc. Sections of such a spiral are sections of concentric circles. Each hologram may have a size of about 2,000 to 100,000 $\mu m^2$ or alternatively of about 7,000 to 80,000 $\mu m^2$, and store data with a density of about 30 to 500 kb/mm$^2$. The holograms may each have a length and a width of 100 to 300 $\mu m$.

The hologram master is then transferred either directly or indirectly onto foil, sheet metal or a shim. For example, the hologram master may be transferred onto a nickel shim by electroforming. Then, several replicas can be made to be used as a stamper for a mass replication process. A replica may be made by injection molding or hot embossing, for example, but roll-to-roll embossing is preferred. For example, the foil or a shim can be placed onto a drum and then used to emboss a multitude of identical holograms on a strip, preferably made of a curable resin. The strip may be made of a polyester resin, especially a resin based on polyethylene terephthalate or an acrylic resin or any other suitable polymer. Strips can be cut into labels such as single separate labels of the same size and shape or can be used as "endless" labels that are attached to laminated bands to be cut into singular test strips so that such individual test strip has a portion of the endless band attached.

It is possible to use only a single hologram master, which is copied repeatedly onto a strip so that a series of copies is created that follow consecutively one after the other. It also is possible to use different hologram masters that are copied alternately onto a strip. For example, holograms may be copied onto a strip by roll-to-roll embossing, wherein half the circumference of the embossing roll is assigned to a first hologram master and a second half of the circumference to a second hologram master. The hologram masters are made to differ in the location where an image appears when the holograms are illuminated. If a strip containing alternating copies of such two hologram masters is illuminated by a spot of laser light such that the spot covers some holograms of a copy of the first hologram master and some holograms of a copy of the second hologram master, then a first image will appear in a first location and a second image in a second location. Thereby, the reading process is not disturbed even by reading from two adjacent copies at the same time. Different sensors or different parts of a sensor area can then be used to capture the two images that contain the same information but appear in different places. If a spot of laser light hits only holograms of a single copy, only a single image is created, which can be read without problems.

Figure 6:
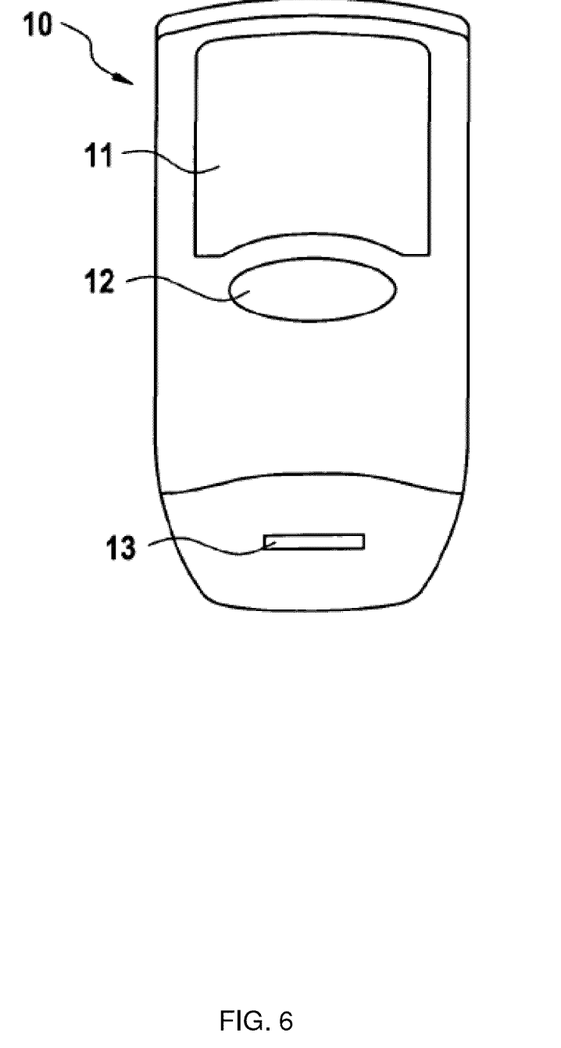
FIG. 6 shows an example of a device for measuring and analyte concentration of a sample with the test element shown in FIG. 1.

FIG. 6 shows a measuring device 10, which together with such test elements forms a measuring system for measuring an analyte concentration of a human or animal body fluid. The measuring device 10 has a display 11 and at least one operating element 12, for example, a key, and an opening 13 for receiving a test element. Such measuring devices are known, for example, for measuring the concentration of glucose, lactate or other analytes and therefore need not be described in detail.

Figure 7:
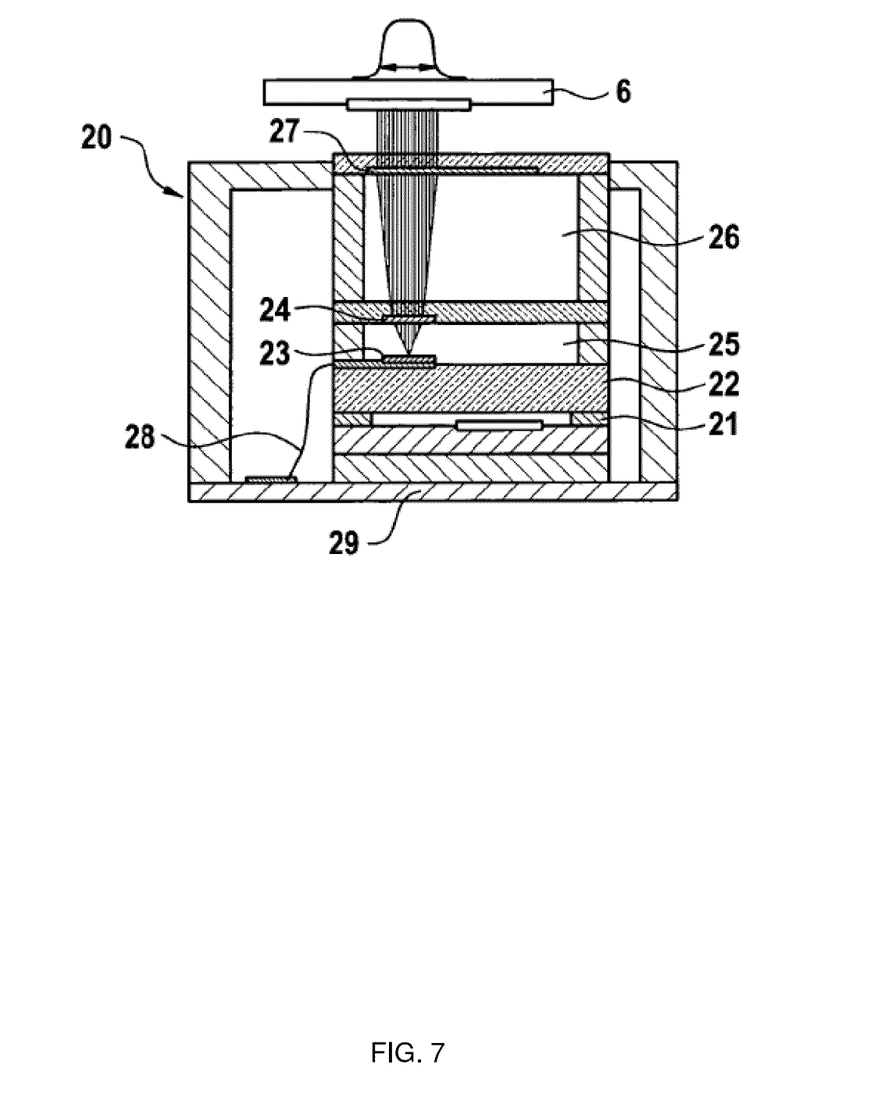
FIG. 7 shows schematically the hologram reader of the device shown in FIG. 6.

The measuring device 10 includes a measuring unit for analyzing the result of a detection reaction of the test field of a test element. The measuring unit may be, for example, a photometric unit or an electric unit adapted to an electrochemical test element. The measuring device also comprises a hologram reader for reading information stored in the hologram of a test element 1. The reader is schematically shown in FIG. 7.

The hologram reader 20 comprises an optical sensor with an array of photosensitive elements such as, for example, a CMOS sensor. The higher the number of photosensitive elements, the higher is the number of bits that can be read from the holographic data storage of a test element 1. In principle, it is sufficient to have one photosensitive element for each dot of the hologram image. However, reading errors can be reduced if the number of photosensitive elements is larger than the number of dots of the hologram image. Preferably, the number of photosensitive elements is at least three times larger or alternatively at least five times larger than the number of dots of the hologram image. In this manner, interference among dots can be avoided. The number of photosensitive elements may be more than ten times larger than the number of dots of the hologram image, especially more than 50 times larger or even more than a hundred times larger. In the example shown, the sensor 21 comprises a 640 by 480 matrix of sensitive elements, and the hologram image a 6 by 25 matrix of dots. The hologram image may contain a larger number of dots, preferably more than 1000 bits, for example, a 60 by 25 matrix of dots. For example, VGA sensors may be used.

The sensor 21 can be connected to a circuit board 21 by a ball grid array. The sensor 21 is covered by a transparent protective layer 22. One or several lasers, preferably two lasers, are placed on the protective layer 22. The laser(s) 23 (e.g., Vertical Cavity Surface Emitting Lasers (VCSEL)), are placed to the side of the array of sensitive elements. This means that the laser(s) 23 are placed outside of the sensor's sensitive area. The laser(s) 23 may be connected to a circuit board 29 by means of a flex connector 28. Each laser 23 is covered by a beam shaping lens 24 that narrows the angle of beam spread.

Adjacent to the laser(s) 23, the protective layer 22 is covered by a spacer layer 25. Both the spacer layer 25 and the lens 24 are covered by another spacer layer 26. The spacer layer 26 is covered by a collimating lens 27. The lenses 24, 27 are diffractive lenses (e.g., Fresnel lenses), but may also be refractive lenses.

Light emitted by laser 23 leaves the reader 20 through the collimating lens 27 for illuminating a spot on a holographic data storage. The diameter of a laser beam after passing through the collimating lens 27 is much smaller than the holographic data storage 6 of a consumable 1, usually less than one fifth. On the other hand, the beam diameter is larger, for example, five or more times larger, than the edge length of one of the holograms 7 of which the holographic data storage consists. In the embodiment shown, the diameter of the collimated beam is 400 to 800 μm, the edge length of a hologram 7 is about 60 to 200 μm and the edge length of the holographic data storage 6 is about 2 mm to 10 mm. The laser 23 preferably illuminates at least 10 or alternatively at least 20 or more, identical holograms of the holographic data storage, which typically contains more than 100 or alternatively more than 500 holograms.

Figure 8:
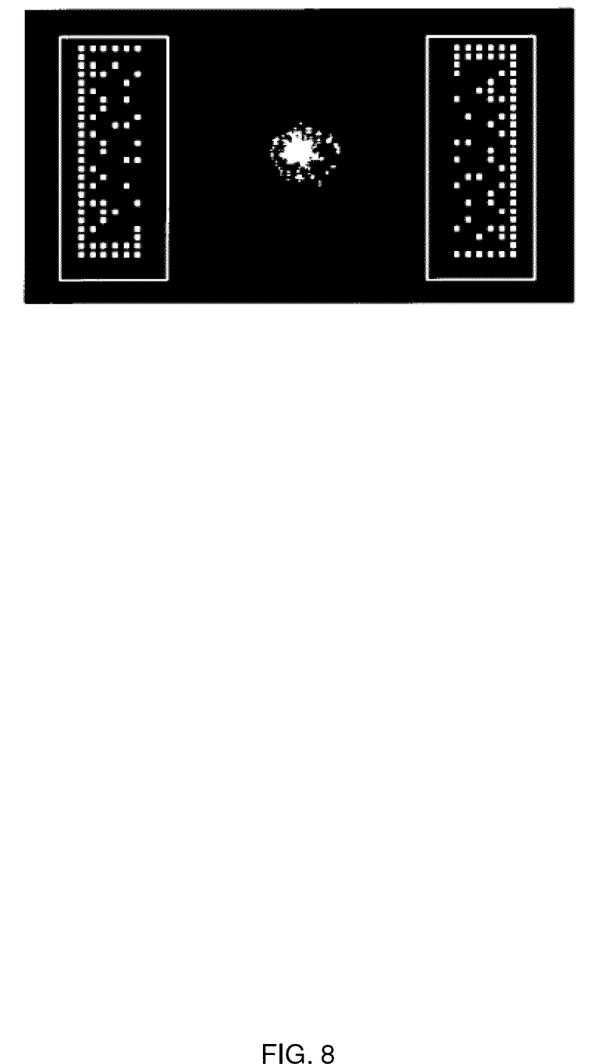
FIG. 8 shows an example of optical signals caused by a laser beam illuminating the holographic data storage of the test element.
Figure 9:
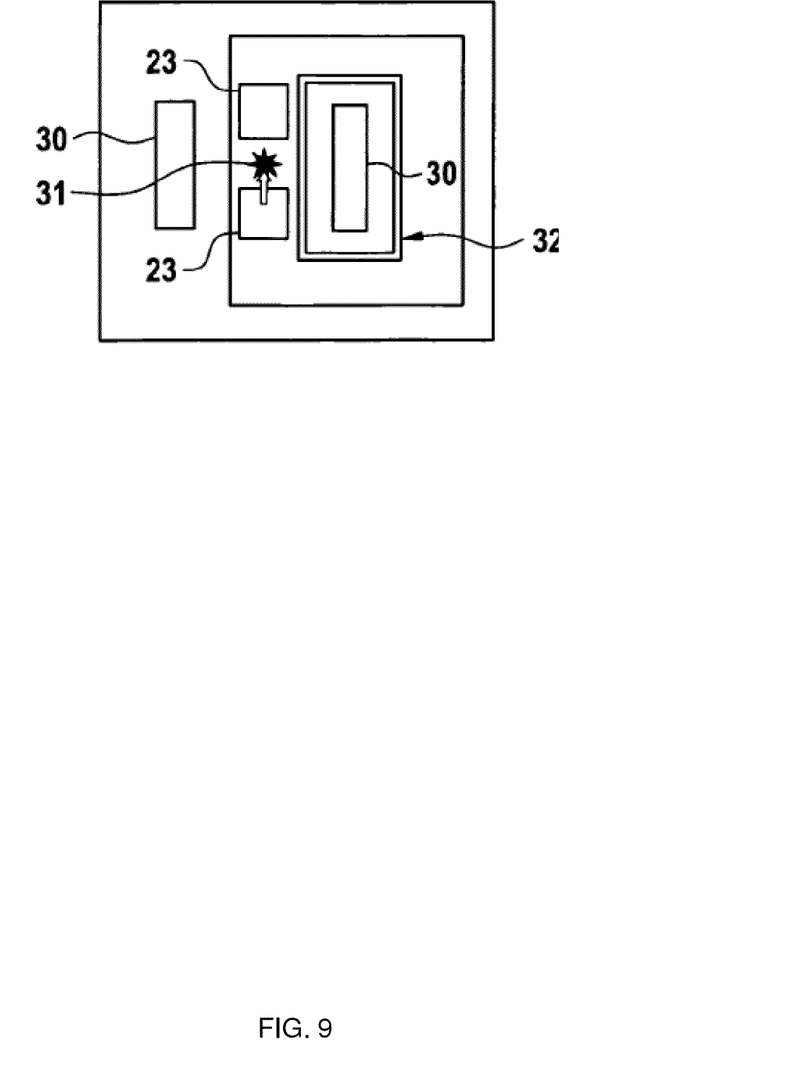
FIG. 9 shows schematically the optical signal of FIG. 8 with respect to the sensor and the laser.

The laser beam is reflected and diffracted by the holographic memory. After reflection and diffraction, the beam enters the reader through the lens 27. FIG. 8 shows an example of optical signals caused by a laser beam illuminating the holographic data storage of the consumable. FIG. 9 shows schematically the optical signals in relation the lasers 23 and the active area of the sensor 21. The holographic image of the holograms may be, for example, a dot matrix.

The holographic memory diffracts the beam similar to an optical grating. The holographic image, and therefore the information stored in the hologram, is in the first maximum of diffraction. Between these images is a specular reflection that contains no useful information.

FIG. 9 shows schematically the holographic images 30 and the specular reflection 31 between them. Also shown are schematically two lasers 23 and the sensitive area 32 of the sensor 21 (i.e., the outline of the array of sensitive elements). The lasers 23 illuminate different spots on the holographic data storage and thereby create each a holographic image. As such, the chance is increased that at least one of the holograms of the holographic memory can be read (i.e., that its holographic image can be captured by the sensor 21). Preferably, the holographic data storage is read by switching only one laser on to create a first image, then switching this laser off and the other laser on to create a second image. Blurring effects and interferences between images from different spots are thereby prevented.

It is usually sufficient to switch each laser on for a time of only 20 to 30 ms to allow the sensor to capture the holographic image. The sensor data should be evaluated before the next laser is turned on. Data evaluation typically takes 0.3 to 0.6 seconds. As such, the holographic data storage can be read in less than 2 seconds, usually even in 1 second or less.

The intensity maximum 31 between the two holographic images 30 is arranged between the lasers 23. This can be achieved by tilting the optical axis of the beam shaping lens 24 with respect to the optical axis of lens 27. The angle of tilting may be 1° to 5° or alternatively 2° to 4°.

The lens 24 is arranged such that geometrical lines defined by the peripheral rays of the beam cone going from the lens 24 to the hologram intersect behind the plane of the sensor 21 when seen from the lens 24. With respect to lens 27, the beam therefore appears to originate from a point that is as far away from lens 27 as the sensor 21. Hence, the specular reflection of the hologram is well focused in the geometric plane of the sensor and far away from the holographic image. Thereby, noise is minimized, which otherwise would interfere with the capturing of the holographic image by the sensor's array of sensitive elements.

The hologram reader also may comprise a microcontroller. The microcontroller may process an adjustment signal which is stored in the holographic data storage together with calibration information of the test field 3. The adjustment signal can be used by the microcontroller for adjusting the power of the lasers 23 to improve the signal to noise ratio and/or contrast. The microcontroller can be integrated into the sensor 21 or can be placed on the same circuit board as the sensor 21.

The microcontroller can process image data. By reading and interpreting image data provided by the sensor 21, the microcontroller can retrieve data stored in the holographic data storage and provide them in easily accessible form. Processing image data provided by the sensor 21 has the advantage of data compression as the holographic data has much less volume than the image data provided by the sensor. Thereby a much smaller data volume has to be transmitted from the reader to other units of the measuring device 10.

The microcontroller also can be used to control acquisition parameters of the sensor, especially integration time. It also is advantageous to control the laser power to, for example, counter laser aging or for security reasons. The microcontroller may also be used to limit power consumption by switching the laser on only during the effective or operative duty cycle. Laser power usually is in the μW range like 1 to 100 μW.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

LIST OF REFERENCE NUMBERS

1 Consumable
2 Substrate
3 Field
4 Cover film
5 Spacer
6 Data Storage
7 Holograms
10 Measuring device
11 Display
12 Operating element 13 Opening
20 Hologram reader
21 Sensor
22 Protective layer
23 Laser
24 Shaping lens
25 Spacer layer
26 Spacer layer
27 Collimating lens
28 Connector
29 Circuit board
30 Holographic images
31 Specular reflection
32 Sensitive area of sensor

The invention claimed is:

1. A test element for measuring an analyte concentration in a human or animal body fluid sample, the test element comprising:
 a substrate carrying a test field with a reagent for effecting a detection reaction when exposed to the body fluid sample; and
 a holographic data storage in which data regarding the test strip is stored, wherein the holographic data storage comprises a plurality of holograms, each containing identical data regarding the test strip, and the plurality of holograms comprising holograms of a first kind and holograms of a second kind, and wherein illumination of the holograms of the first kind causes an image in a first location and illumination of the holograms of the second kind causes an image in a second location.

2. The test element of claim 1, wherein the holographic data storage comprises digital holograms.

3. The test element of claim 1, wherein the data stored by the holographic data storage is encoded in a two-dimensional dot matrix.

4. The test element of claim 1, wherein the holographic data storage is written by pixels that are arranged along sections of parallel arcs.

5. A medical product comprising a holographic data storage in which data regarding the product is stored, wherein the holographic data storage comprises a plurality of holograms each containing identical data regarding the medical product, the plurality of holograms comprising holograms of a first kind and holograms of a second kind, and wherein illumination of the holograms of the first kind causes an image in a first location and illumination of the holograms of the second kind causes an image in a second location.

6. The medical product of claim 5, wherein the holographic data storage is imprinted directly on the medical product.

7. The medical product of claim 6, further comprising a label comprising the holographic data storage.

8. The medical product of claim 5, wherein the data contains batch-specific data.

* * * * *